US005631348A

United States Patent [19]

Rosenblum et al.

[11] Patent Number: 5,631,348

[45] Date of Patent: May 20, 1997

[54] PROTEIN SEQUENCE OF THE PLANT TOXIN GELONIN

[75] Inventors: Michael Rosenblum, Houston, Tex.; William J. Kohr, San Mateo, Calif.; Bharat Aggarwal, Houston, Tex.

[73] Assignee: The Research Development Foundation, Carson City, Nev.

[21] Appl. No.: 254,662

[22] Filed: Jun. 6, 1994

Related U.S. Application Data

[63] Continuation of Ser. No. 119,899, Sep. 10, 1993, abandoned, which is a continuation of Ser. No. 908,959, Jul. 6, 1992, abandoned, which is a continuation of Ser. No. 567,220, Aug. 14, 1990, abandoned.

[51] Int. Cl.$^6$ .......................... C07K 14/415; C12N 15/29

[52] U.S. Cl. .......................... 530/370; 536/23.6

[58] Field of Search .......................... 536/23.6; 530/370; 435/172.3, 252.3

[56] References Cited

U.S. PATENT DOCUMENTS

| | | | |
|---|---|---|---|
| 4,446,240 | 5/1984 | Nerenberg | 436/542 |
| 4,810,648 | 3/1989 | Stalker | 435/191 |
| 4,888,415 | 12/1989 | Lambert et al. | 530/390 |
| 4,921,802 | 5/1990 | Hall et al. | 435/172.3 |

OTHER PUBLICATIONS

Lambert et al., *Cancer Treat. Res.*, vol. 37, 1988, pp. 175–209.
Ronneberger, *Dev. Biol. Stand.*, vol. 71, 1990, pp. 185–190.
Benoit et al., *Curr. Eye Res.*, vol. 9 Suppl., 1990, pp. 201–205.
Roselli et al., *J. Nuclear Med.*, vol. 30, 1989, pp. 672–682.
Dunbar, *Two-Dimensional Electrophoresis and Immunological Techniques*, 1987, Plenum Press, New York, pp. 32–34.
Stirpe et al., *J. Biol. Chem.* v. 255, 1980, pp. 6947–6953.
Jacobs, et al., *Nature* v. 313, 1985, pp. 806–810.
Falasca et al., *Biochem. J.* v. 207, 1982, pp. 505–509.
Sivam et al., *Cancer Res.* v. 47, 1987, pp. 3169–3173.
Young et al., *Science* v. 222, 1983, pp. 778–782.
Toy, J. L., *Clin. Exp. Immunol.*, 1983, 54, 1–13.

*Primary Examiner*—James S. Ketter
*Attorney, Agent, or Firm*—Benjamin Aaron Adler

[57] ABSTRACT

This invention relates to substantially purified gelonin, toxic fragments thereof, the DNA sequences encoding gelonin and use of the DNA for producing, by recombinant technology, gelonin, toxic fragments thereof and fusion proteins. More specifically, the invention relates to the primary amino acid sequence of gelonin, and of the DNA encoding said gelonin and the production of synthetic gelonin and toxic fragments thereof.

2 Claims, 13 Drawing Sheets

```
  1        10        20        30        40        50        60        70
  |        |         |         |         |         |         |         |
GLDTVSFSTKGATYITYVNFLNELRVKLKPEGNSHGIPLLSKGDDPGKCFVLVALSNDNGQLAEIAIDVT
―――――――N-TERMINAL―――――――                ――Lys-c(RCM)―→―   ―LimLys-c―    ――HYDROX.Am.

 71       80        90       100       110       120       130       140
  |        |         |         |         |         |         |         |
SVYVVGYQVRNRSYFFKDAPDAAYEGLFKNTIKNPLLFGGKTRLHFGGSYPSLEGEKAYRETTDLGIEPL
         ――→―Lys-c―→  ―V8―              ――――Lys-c――――      V8―200―→  V8 210

141      150       160       170       180       190      200       210
  |        |         |         |         |         |         |         |
RIGIKKLDENAIDNYKPTEIASSLLVVIQMVSEAARFTFIENQIRNNFQQRIRPANNTISLENKWGKLSF
―Lys-c―   ―――Lys-c―――                     ―――CNBr―――

211      220       230       240       250
  |        |         |         |         |
QIRTSGANGMFSEAVELERANGKKYYVTAVDQVKPKIALLKFVDKDPE
  ―――TD-(RCM)―――→  ―CNBr+Ms――――――――――――――→
```

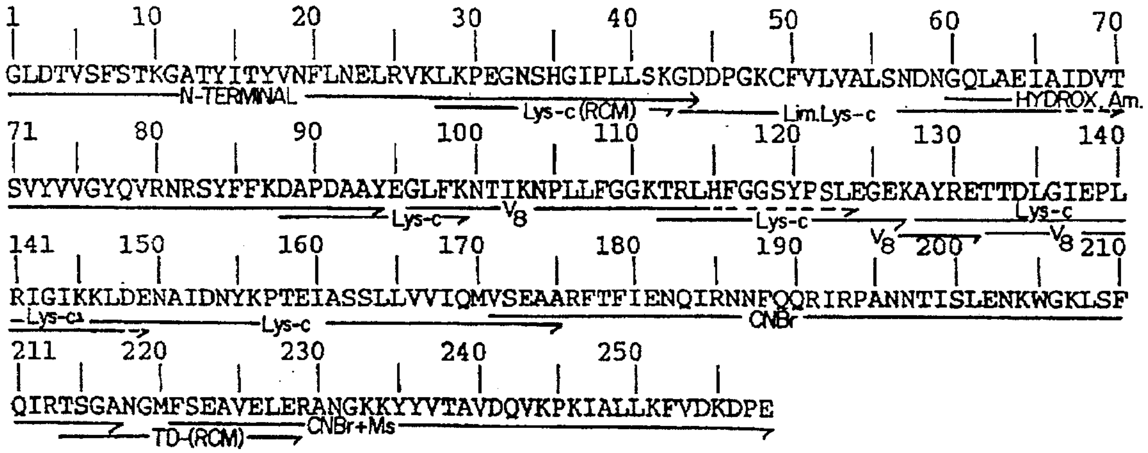

FIG. 1

```
  1 GGNYTNGAYA CNGTNWSNTT YWSNACNAAR GGNGCNACNT AYATHACNTA
    CCNRANCTRT GNCANWSNAA RWSNTGNTTY CCNCGNTGNA TRTADTGNAT
    GlyLeuAspT hrValSerPh eSerThrLys GlyAlaThrT yrIleThrTy

                                                    ecoRI
 51 YGTNAAYTTY YTNAAYGARY TNMGNGTNAA RYTNAARCCN GARGGNAAYW
    RCANTTRAAR RANTTRCTYR ANKCNCANTT YRANTTYGGN CTYCCNTTRW
    rValAsnPhe LeuAsnGluL euArgValLy sLeuLysPro GluGlyAsnSer

          ecoRI
101 SNCAYGGNAT HCCNYTNYTN WSNAARGGNG AYGAYCCNGG NAARTGYTTY
    SNGTRCCNTA DGGNRANRAN WSNTTYCCNC TRCTRGGNCC NTTYACRAAR
       HisGlyIl eProLeuLeu SerLysGlyA spAspProGl yLysCysPhe

151 GTNYTNGTNG CNYTNWSNAA YGAYAAYGGN CARYTNGCNG ARATHGCNAT
    CANRANCANC GNRANWSNTT RCTRTTRCCN GTYRANCGNC TYTADCGNTA
    ValLeuValA laLeuSerAs nAspAsnGly GlnLeuAlaG luIleAlaIle

201 HGAYGTNACN WSNGTNTAYG TNGTNGGNTA YCARGTNMGN AAYMGNWSNT
    DCTRCANTGN WSNCANATRC ANCANCCNAT RGTYCANKCN TTRKCNWSNA
     AspValThr SerValTyrV alValGlyTy rGlnValArg AsnArgSerT

251 AYTTYTTYAA RGAYGCNCCN GAYGCNGCNT AYGARGGNYT NTTYAARAAY
    TRAARAARTT YCTRCGNGGN CTRCGNCGNA TRCTYCCNRA NAARTTYTTR
    yrPhePheLy sAspAlaPro AspAlaAlaT yrGluGlyLe uPheLysAsn

301 ACNATHAARA AYCCNYTNYT NTTYGGNGGN AARACNMGNY TNCAYTTYGG
    TGNTADTTYT TRGGNRANRA NAARCCNCCN TTYTGNKCNR ANGTRAARCC
    ThrIleLysA SnProLeuLe uPheGlyGly LysThrArgL euHisPheGl

351 NGGNWSNTAY CCNWSNYTNG ARGGNGARAA RGCNTAYMGN GARACNACNG
    NCCNWSNATR GGNWSNRANC TYCCNCTYTT YCGNATRKCN CTYTGNTGNC
    yGlySerTyr ProSerLeuG luGlyGluLy sAlaTyrArg GluThrThrAsp

401 AYYTNGGNAT HGARCCNYTN MGNATHGGNA THAARAARYT NGAYGARAAY
    TRRANCCNTA DCTYGGNRAN KCNTADCCNT ADTTYTTYRA NCTRCTYTTR
      LeuGlyIl eGluProLeu ArgIleGlyI leLysLysLe uAspGluAsn

451 GCNATHGAYA AYTAYAARCC NACNGARATH GCNWSNWSNY TNYTNGTNGT
    CGNTADCTRT TRATRTTYGG NTGNCTYTAD CGNWSNWSNR ANRANCANCA
    AlaIleAspA snTyrLysPr oThrGluIle AlaSerSerL euLeuValVal

501 NATHCARATG GTNWSNGARG CNGCNMGNTT YACNTTYATH GARAAYCARA
    NTADGTYTAC CANWSNCTYC GNCGNKCNAA RTGNAARTAD CTYTTRGTYT
     IleGlnMet ValSerGluA laAlaArgPh eThrPheIle GluAsnGlnI

551 THMGNAAYAA YTTYCARCAR MGNATHMGNC CNGCNAAYAA YACNATHWSN
    ADKCNTTRTT RAARGTYGTY KCNTADKCNG GNCGNTTRTT RTGNTADWSN
    leArgAsnAs nPheGlnGln ArgIleArgP roAlaAsnAs nThrIleSer

601 YTNGARAAYA ARTGGGGNAA RYTNWSNTTY CARATHMGNA CNWSNGGNGC
    RANCTYTTRT TYACCCCNTT YRANWSNAAR GTYTADKCNT GNWSNCCNCG
    LeuGluAsnL ysTrpGlyLy sLeuSerPhe GlnIleArgT hrSerGlyAl
```

FIG. 2A

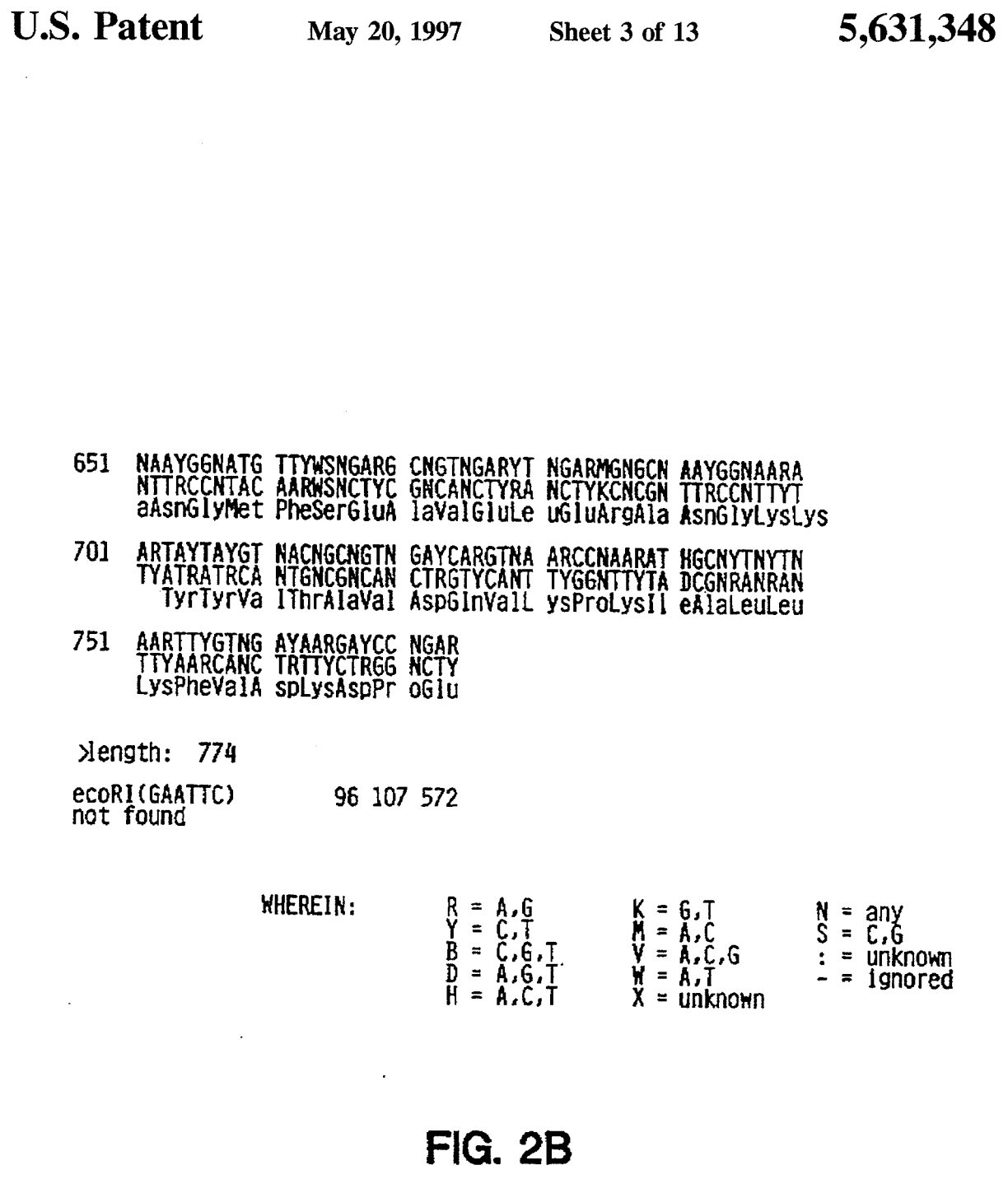

```
651  NAAYGGNATG TTYWSNGARG CNGTNGARYT NGARMGNGCN AAYGGNAARA
     NTTRCCNTAC AARWSNCTYC GNCANCTYRA NCTYKCNCGN TTRCCNTTYT
     aAsnGlyMet PheSerGluA laValGluLe uGluArgAla AsnGlyLysLys

701  ARTAYTAYGT NACNGCNGTN GAYCARGTNA ARCCNAARAT HGCNYTNYTN
     TYATRATRCA NTGNCGNCAN CTRGTYCANT TYGGNTTYTA DCGNRANRAN
       TyrTyrVa lThrAlaVal AspGlnValL ysProLysIl eAlaLeuLeu

751  AARTTYGTNG AYAARGAYCC NGAR
     TTYAARCANC TRTTYCTRGG NCTY
     LysPheValA spLysAspPr oGlu

>length: 774

ecoRI(GAATTC)        96 107 572
not found
```

WHEREIN:

| | | |
|---|---|---|
| R = A,G | K = G,T | N = any |
| Y = C,T | M = A,C | S = C,G |
| B = C,G,T | V = A,C,G | : = unknown |
| D = A,G,T | W = A,T | - = ignored |
| H = A,C,T | X = unknown | |

FIG. 2B

```
gelonin  1    ------------------------------GLDTVSFSTKGATYITYVNFLN
tricho   1    ----------------------------DVSFRLSGATSSSYGVFIS
abrin    1    ---------------------------QDRPIKFSTEGATSQSYKQFIE
ricin    1    -----------------------IFPKQYPIINFTTAGATVQSYTNFIR
agg      1    MYAVATWLCFGSTSGWSFTLEDNNIFPKQYPIINFTTADATVESYTNFIR

gelonin  23   ELRVKLKPEGN-SHGIPLL---SKGDDPGKCEVLYALSNDNGQLAEIAIDV
tricho   20   NLRKALPNERKL-YDIPLL--PSSLPGSDRYALTHLINYADETISVAIDV
abrin    23   ALRERLRGG--LIHDIPVLPDPTTLQERNRYITVELSNSDTESIEVGIDV
ricin    27   AVRGRLTTGADVRHEIPVLPNRVGLPINQRFILVELQNHAELSVTLALDV
agg      51   AVRSHLTTGADVRHEIPVLPNRVGLPISQRFILVELSNHAELSVTLALDV

gelonin  70   TSVYVVGYQVRNRSYFFK---DAPDAAYEGLFKNTIKNPLLFGGKTRLHF
tricho   67   TNVYIMGYRAGDTSYFFN--EASATEAAKYVFKDAMR-------KVILPY
abrin    71   TNAYVVAYRAGTQSYFLR--DAPSSASDYLFTGTDQ-------H-SLPF
ricin    77   TNAYVVGYRAGNSAYFFHPDNQEDAEAITHLFTDVQN-------RYTFAF
agg      101  TNAYVVGCRAGNSAYFFHPDNQEDAEAITHLFTDVQN-------SHTFAF

gelonin  117  GGSYPSLEG-EKAYRETDLGIEPLRIGIKKLDENAIDNYKPTEIASSLL
tricho   108  SGNYERLQTAAGKIRENIPLGLPALDSAITTLFYYNANSA-----ASALM
abrin    110  YGIYGDLERWAHQSRQQIPLGLQALTHGIS---FFRSGGNDNEEKARTLI
ricin    120  GGNYDRLEQLAGNLRENIELGNGPLEEAISALYYYSTGGTQLPTLARSFI
agg      144  GGNYDRLEQLGG-LRENIELGTGPLEDAISALYYYSTCGTQIPTLARSFM

gelonin  166  VMIQMVSEAARFTFIENQIRNN---FQQRIRPANNTISLENKWGKLSFQIR
tricho   153  VLIQSTSEAARYKFIEQQIGKRV--DKTFLPSLAIISLENSWSALSKQIQ
abrin    157  MIIQMVAEAARFRYISNRVRVSTQTGTAFQPDAAMISLENNWDNLR-GVQ
ricin    170  ICIQMISEAARFQYIEGEMRTRIRYNRRSAPDPSVITLENSWGRLSTAIQ
agg      193  VCIQMISEAARFQYIEGEMRTRIRYNRRSAPDPSVITLENSWGRLSTAIQ

gelonin  214  -TSGANGMFSEAVEL--ERANGKKYYMTAVDQVKPKIALLKFVDKDE--
tricho   201  IASTINGQFESPVMLINAQNQRVTITNVDAGVMTSNI-ALLLNRNNMA--
abrin    206  --ESVQDTFPNQMTLLIRNIRNEPVIVDSLSHPTVAVLA-LMLFVQNPRN--
ricin    220  --ESNQGAFASPIQL---QRDGSKFSVYDVSILIPII-AMVYRCAPPPSS
agg      243  --ESNQGAFASPIQL--QRRNGSKFNVYDVSILIPIIALMVYRCAPPPSS
```

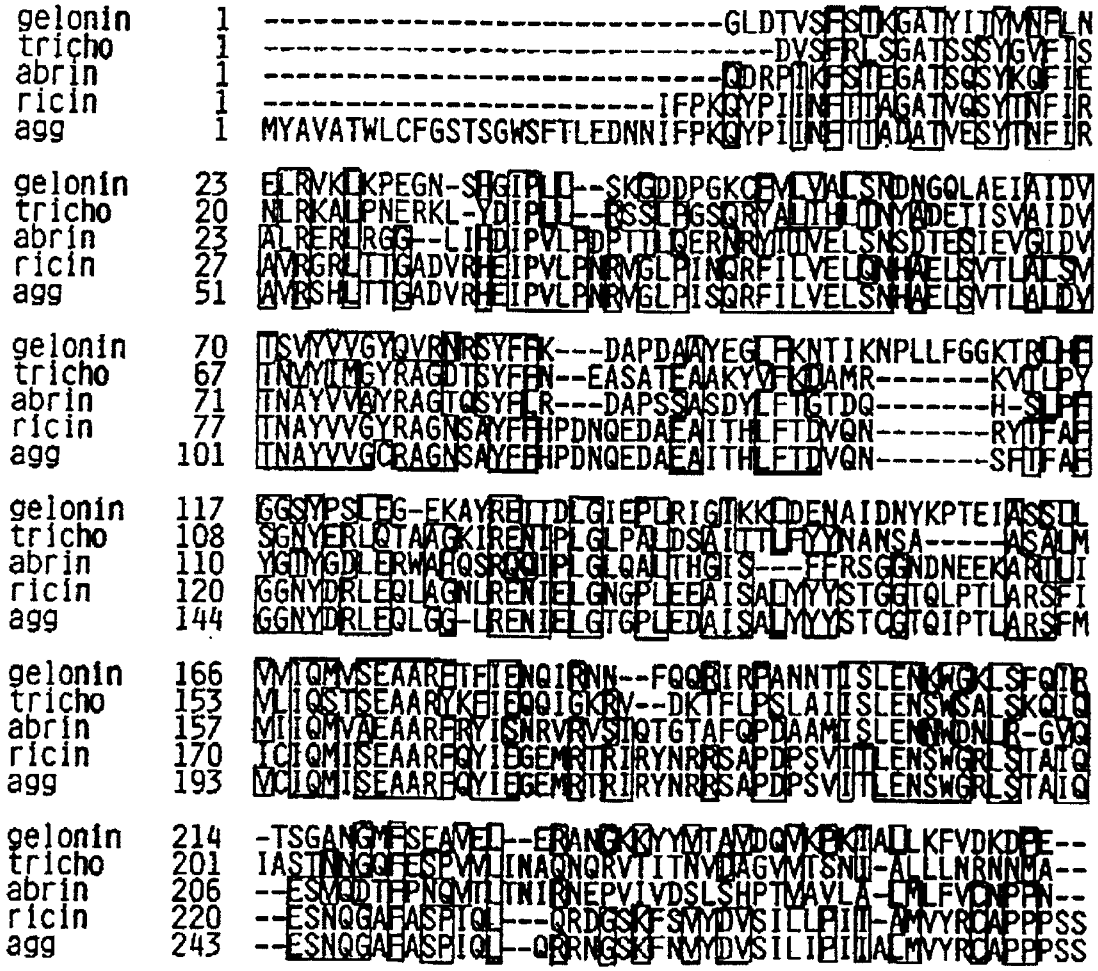

FIG. 3

PROTEIN SEQUENCE OF THE PLANT TOXIN GELONIN

This is a continuation of application Ser. No. 08/119,899 filed on Sep. 10, 1993, now abandoned, which is a continuation of U.S. Ser. No. 07/908,959 filed Jul. 6, 1992, abandoned, which is a continuation of U.S. Ser. No. 07/567,220, filed Aug. 14, 1990, now abandoned.

TECHNICAL FIELD

This invention relates to substantially purified gelonin, toxic fragments thereof, the DNA sequences encoding gelonin and use of the DNA for producing, by recombinant technology, gelonin, toxic fragments thereof and fusion proteins. More specifically, the invention relates to the primary amino acid sequence of gelonin, and of the DNA encoding said gelonin and the production of synthetic gelonin and toxic fragments thereof.

BACKGROUND ART

A major challenge for the design of a drug for treatment of any disease is specificity and efficacy. Various drugs available for the treatment of cancer suffer from problems of this nature. The concept of targeting toxic drugs selectively to certain tumors has been a subject of intense research in the last few years (Thorpe (1985) *Biol Clin Applications* 84:475–512; Moller ed. (1982) *Immun. Rev.* 62:1–215). Recently both monoclonal and polyclonal antibodies, lectins, lymphokines and hormones which recognize specific determinants on the surface of the tumor cell have been used as carriers to deliver toxic agents into the cell, where the latter can exert their cytotoxic potential (Blattler, et al. (1985) *Biochemistry* 24:1517–1524; Frankel, et al. (1985) *J. Biol, Res, Modif,* 4:437–446; Reimann, et al. (1988) *J. Clin. Invest.* 82:129–138; Schwartz and Vale (1988) *Endocrinology* 122:1695–1700; Scott, et al. (1987) *J Natl. Cancer Inst.* 79:1163–1172; Singh, et al. (1989) *Biol. Chem.* 264:3089–3095; Srinivasan, et al. (1985) *FEBS Letters* 192:113; Schwartz, et al. (1987) *Endocrinology* 121:1454–1460). Toxic moieties thus far investigated with these delivery agents include radionuclides (Ghose, et al. (1967) *Br, Med, J.* 1:90–96), cytotoxic drugs commonly employed in cancer chemotherapy (Thorp and Ross (1982) *Immun. Rev,* 62:119–157; Deweger, et al. (1982) *Immun. Rev.* 62:29–45; Arnon and Sela (1982) *Immun. Rev.* 62:5–27; Pimm, et al. (1982) *Cancer Immun. Immunotherap,* 12:125–134; Rowland and Axton (1985) *Cancer Immun. Immunotherap.* 19:1–7) and proteins derived from bacteria and plants such as diptheria or ricin (Jansen, et al. (1982) *Immun. Rev.* 62:185–216; Raso (1982) *Immun. Rev.* 62:93–117. Vitetta, et al. (1982) *Immun. Rev,* 62:159–183; Nelville and Youle (1982) *Immun. Rev,* 92:47–73; Thorpe, et al. (1981) *Eur. J. Biochem.* 116:447–454). A specific molecule is designed by replacing the nonspecific B chain with an antibody or a hormone.

Bacterial and plant toxins, such as diphtheria toxin (DT), *Pseudomonas aeruginosa* toxin A, abrin, ricin, mistletoe, modeccin, and Shigella toxin, are potent cytocidal agents due to their ability to disrupt a critical cellular function. For instance, DT and ricin inhibit cellular protein synthesis by inactivation of elongation factor-2 and inactivation of ribosomal 60s subunits, respectively (*Bacterial Toxins and Cell Membranes*, Eds. Jelajaszewicz and Wadstrom (1978) Academic Press, p. 291). These toxins are extremely potent because they are enzymes and act catalytically rather than stoichiometrically. The molecules of these toxins are composed of an enzymatically active polypeptide chain or fragment, commonly called "A" chain or fragment, linked to one or more polypeptide chains or fragments, commonly called "B" chains or fragments, that bind the molecule to the cell surface and enable the A chain to reach its site of action, e.g., the cytosol, and carry out its disruptive function. The act of gaining access to the cytosol is called variously "internalization", "intoxication", or "translocation". These protein toxins belong to a class bearing two chains referred to as A and B chains. The B chain has the ability to bind to almost all cells whereas the cytotoxic activity is exhibited by the A chain. It is believed that the A chain must be timely liberated from the B chain-frequently by reduction of a disulfide bond-in order to make the A chain functional. These natural toxins are generally not selective for a given cell or tissue type because their B chains recognize and bind to receptors that are present on a variety of cells.

The availability of a toxin molecule which is not cytotoxic to a variety of cells when administered alone has been limited. Utilizing certain naturally occurring single chain toxin molecules which do not themselves bind to cell surface receptors and, therefore, are not normally internalized by cells, has provided toxic molecules which are relatively non-toxic to most, if not all, cells when administered alone. Such naturally occurring single chain toxins known to date, include, but are not limited to, pokeweed antiviral protein (Ramakrishnan and Houston (1984) *Cancer Res.* 44:201–208), saponin (Thorpe, et al. (1985) *J. Natl, Cancer Inst.* 75:151–159), and gelonin (Stirpe, et al (1980) *J. Biol. Chem.* 255:6947–6953). These proteins are nontoxic to cells in the free form, but can inhibit protein synthesis once they gain entry into the cell. However, the availability of these single chain toxins in substantially pure form is limited due to the fact that they must be purified from plant sources in which they occur in relatively low amounts and the reproducibility of the concentration of the toxin in the plants is dependent upon plant growth conditions and plant harvest conditions.

Gelonin is a single chain polypeptide isolated from seeds of a plant, *Gelonium multiforum*, having a molecular weight of approximately 28,000–30,000 kd. Gelonin is a basic glycoprotein with an approximate isoelectric point of 8.15 and contains mannose and glucosamine residues (Falasca, et al. (1982) *Biochem J,* 207:505–509). In contrast to other plant and bacterial toxins, this protein is not toxic to cells by itself, but when delivered to cells through a carrier, it damages the 60s ribosomal subunit. In vivo and in vitro biological data suggest that gelonin is equivalent or superior to other plant toxins. In fact, the results of a comparison of gelonin conjugates in vitro and in vivo with other A chain conjugates indicated that gelonin had similar potency, better selectivity, better tumor localization, and more significant therapeutic effects (Sivan, et al (1987) *Cancer Res,* 47:3169–3173). However, the availability of a reproducible, readily accessible supply of gelonin from natural sources is limited. In addition, the purification of gelonin from plant sources is difficult and the yield is very low.

Gelonin by itself has been shown to be abortifacient in mice and enhances antibody dependent cell cytotoxicity (Yeung, et al (1988) *Internatl. J. Peptide Protein Res,* 31:265–268).

Several investigators have utilized gelonin as a cytotoxic agent chemically attached to monoclonal antibodies or to peptide hormone cellular targeting ligands. However, chemical modification of gelonin and cellular targeting moieties can reduce targeting efficiently and cytotoxic potential of gelonin itself. Furthermore, natural sources of gelonin are subject to variability in harvesting and plant growth which can affect gelonin cytotoxic activity. The ability to produce a synthetic gelonin toxin, chemically or utilizing recombinant technology, provides a plentiful, reproducible source of the toxin.

SUMMARY OF THE INVENTION

The present invention provides substantially pure gelonin having the amino acid sequence shown in FIG. 1. The present invention also provides the DNA sequence for gelonin shown in FIG. 2. Utilization of the sequences of the present invention to produce substantially pure gelonin in plentiful amounts by recombinant technology provides abundant amounts of the toxin which were not heretofore available from natural sources.

BRIEF DESCRIPTION OF THE DRAWINGS

FIG. 1 shows the amino acid sequence of gelonin.

FIG. 2 demonstrates the cDNA encoding for gelonin.

FIG. 3 demonstrates the homology of the gelonin amino acid sequence with the sequence of trichosanthin, Ricin A chain, Agglutinin precursor isolated from Castor bean and Abrin A chain.

DETAILED DESCRIPTION OF THE INVENTION

The term "substantially pure" when applied to the gelonin protein of the present invention means that the polypeptide is essentially free of other plant proteins normally associated with the gelonin in its natural state and exhibiting reproducible electrophoretic or chromatographic response, elution profiles, and toxic activity. The term "substantially pure" is not meant to exclude artificial or synthetic mixtures of the gelonin protein with other compounds.

Gelonin was purified from the seeds of the plant *Gilonin multiforum* by techniques known to those of skill in the art. The amino acid sequence was determined utilizing a modification of the Edman degradation method.

Samples of gelonin were applied to the reverse phase reaction chamber and subjected to Edman degradation. The N-terminal of gelonin was found to be heterogeneous (½ of the molecules of the protein were apparently one amino acid shorter than the others). This heterogeneity made it difficult to sequence much more than 40 cycles. Therefore, in order to determine further amino acids in the sequence, enzymatic cleavage was performed.

Internal sequence of proteins is generally obtained by digesting or cutting up the large protein molecule into smaller pieces with a combination of enzymes and chemical cleaveges. When native gelonin was exposed to various protolytic enzyzme digestions, it was found to be incompletely cleaved. This was found to be partly due to a disulfide bond in the N-terminal part of the molecule. Breaking of this bond by reduction and alkylation with iodoacetic acid yielded a fragment that was less soluable than the native material at the pH required for enzymatic digestion. A combination of digestion of native gelonin with trypsin, Lysine aminopeptidase (Lysc), staphlococcal protease (V8), and chymotrypsin yielded peptides mostly from the C-terminal portion of the molecule. This indicated that the N-terminal part of the molecule (from the N-terminal analysis to the Asp-Ala-Pro at residue 70) was not readily accessible by enzyme digestions.

Figure 4:
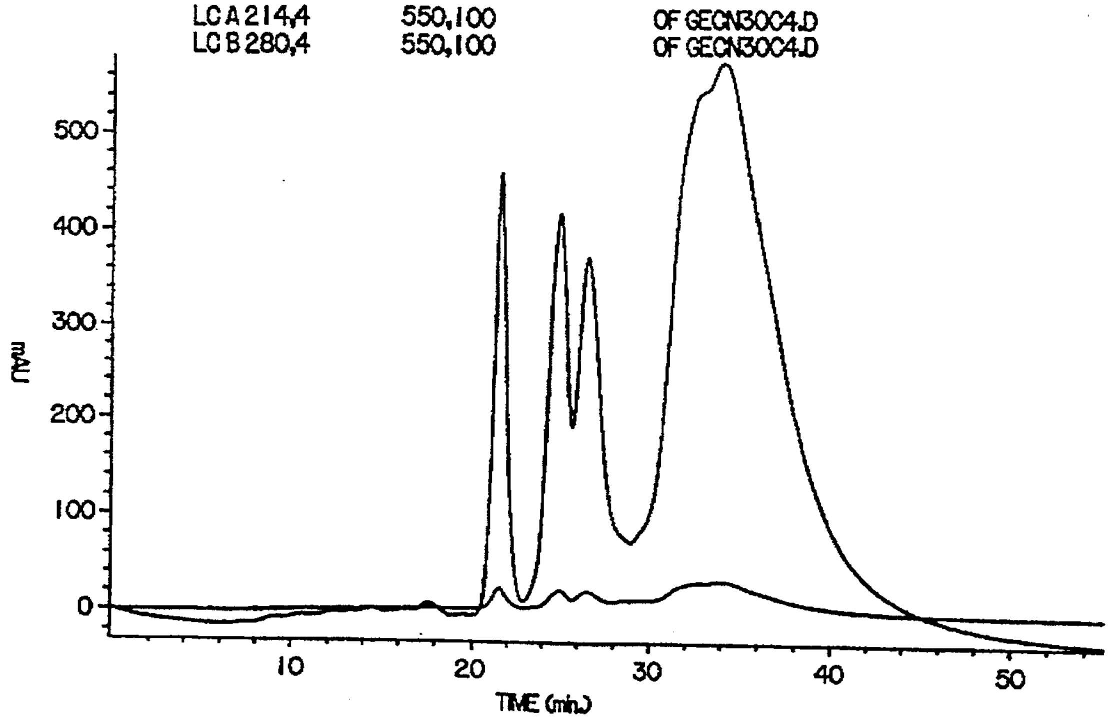
FIG. 4 demonstrates the HPLC profile of CNBr fragments.

Gelonin was cleaved with cyanogen bromide into 3 large peptides. Protein aliquots (0.2 mg/ml) were dissolved in 70% formic acid. A crystal of cyanogen bromide was added to the solution and the reaction allowed to proceed for at least 18 hours. The solution was then diluted with water and was applied to a small sequencing column. After sample application, a gradient of 1% to 10% n-propanol with 0.1% TFA was used to elute the protein fragments. The elution profile is shown on FIG. 4.

Enzymatic digestion of the whole protein or of CNBr fragments yeilded overlapping peptides. Enzymatic digestions with Lysyl endopeptidase in 0.1% SDS 100 mM Tris pH 8.0, Staphylococcus Aureus Protease in 0.1% SDS or trypsin in 0.1% Tween 20 were carried out. Gelonin contains one cysteine residue at position 49. Reduction and carboxymethylation yeilds a protein which recovers better on reverse phase HPLC and is more susceptible to enzymatic digestion. Therefore, most of the enzymatic digestions were carried out in 0.1% SDS or 0.1% Tween.

Figure 5A:
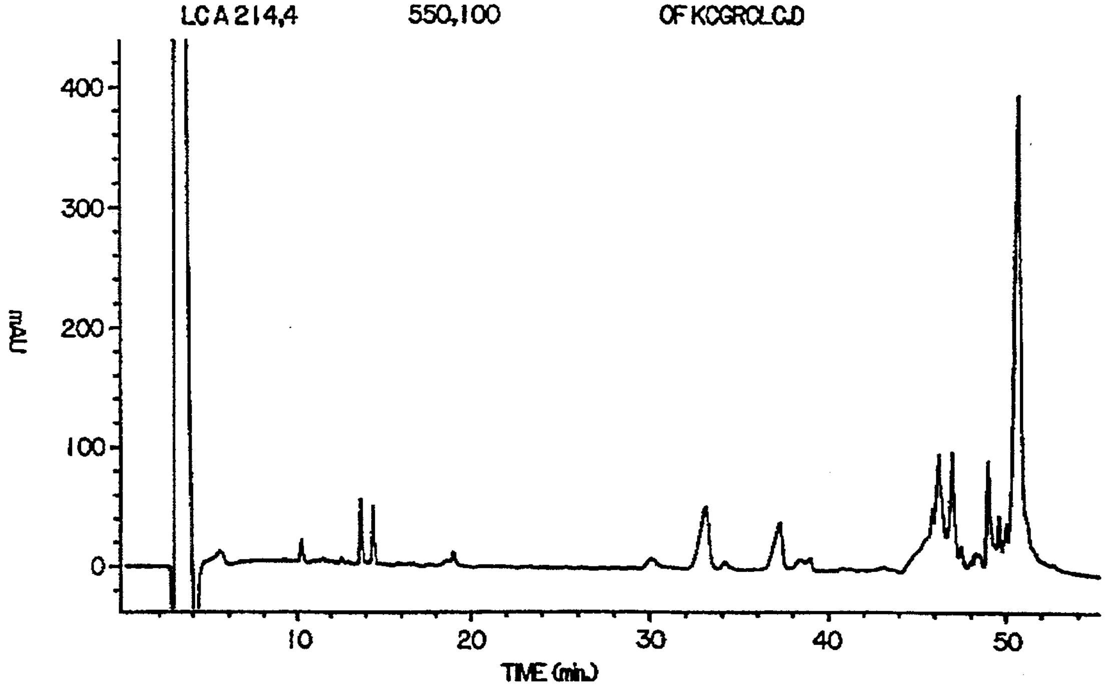
FIGS. 5A, 5B and 5C demonstrates the HPLC profile of (A) Lys-c, (B) Staphyloccus protease, and (C) Hydroxylamine digests of gelonin.
Figure 5B:
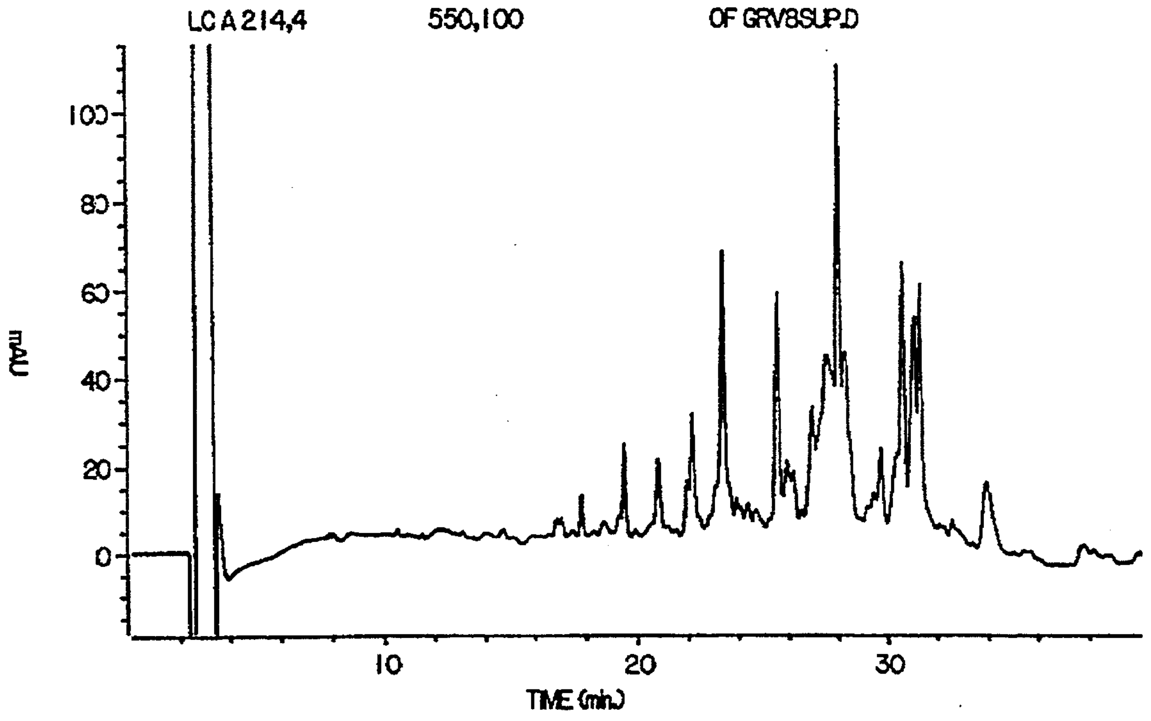

After the C-terminal 160 residues were aligned by a combination of CNBr digests and enzymatic cleaveges. The remaining unknown sequence between residues 40 to 70 was determined by a combination of chemical modification of cysteine with iodoacetic acid and solubization of the alkylated protein with SDS. The RCM alkylated gelonin was then cleaved with excess Lysc enzyme at 37° C. for short periods of time (1–5 hr.). The HPLC elution profile is shown on FIG. 5A.

This method yielded a new sequence that had not been seen before. This new sequence showed the existence of an Asn-Gly combination. This combination of amino acids is cleaveable by a chemical method using hydroxylamine.

Figure 5C:
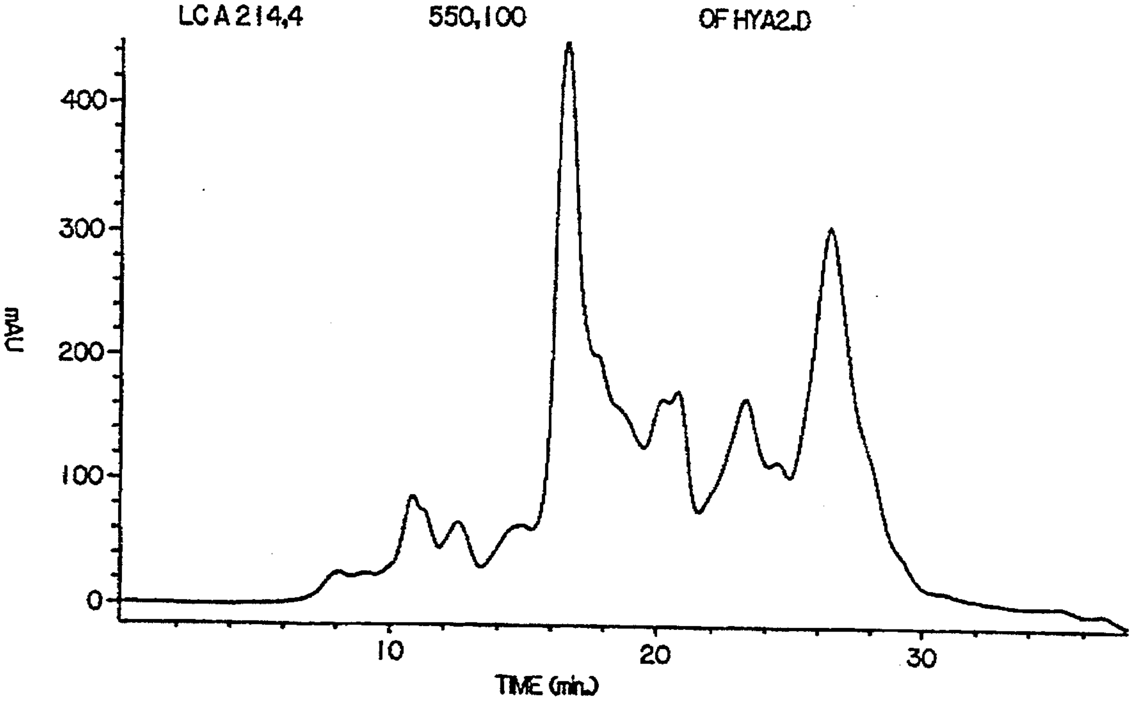
Figure 6A:
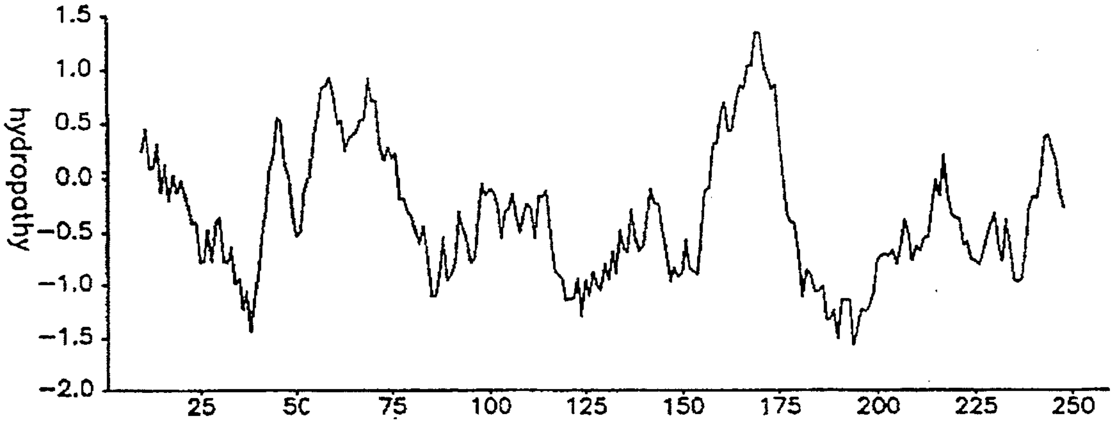
FIGS. 6A, 6B, 6C and 6D demonstrates the hydrophobicity plots of gelonin (A), trichosanthin (B), abrin (C), ricin (D), and agglutinin precursor (E).
Figure 6B:
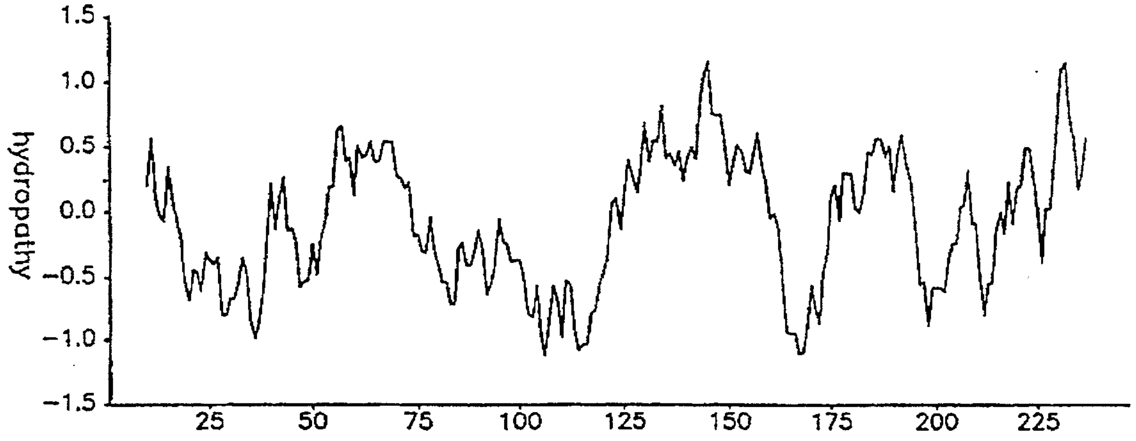
Figure 6C:
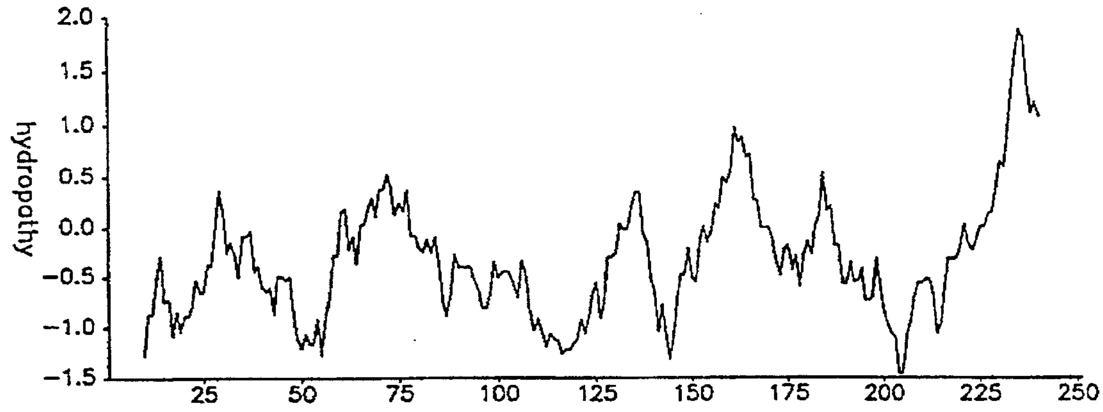
Figure 6D:
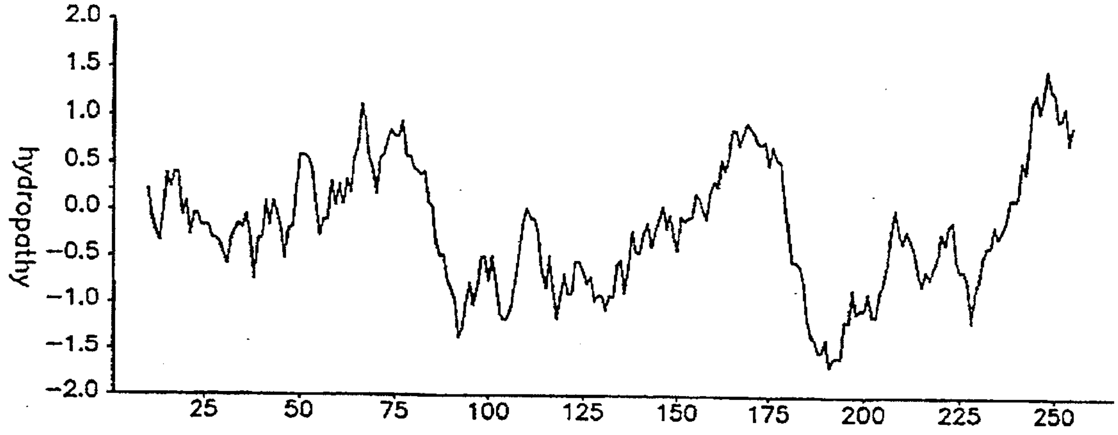
Figure 6E:
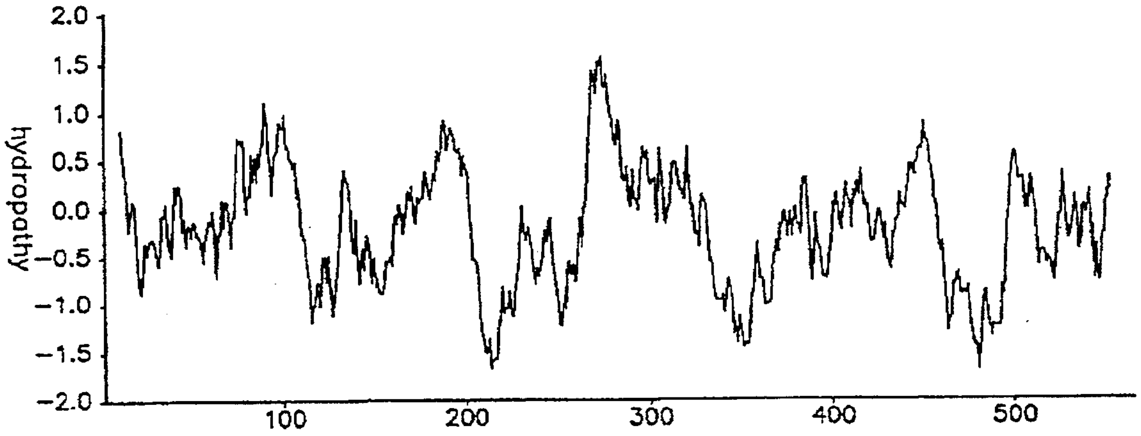

Hydroxylamine cleavage was carried out by adding 100 ug of gelonin to freshly prepared hydroxylamine (2M) in 0.2 M Tris (pH 9.0) with 2M NaCl, mm EDTA and 10% ethanol. After incubation for 7 hours at room temperature, the entire reaction mixture was applied to a sequencing column. The colulmn was then washed with 1% TFA in water and either eluted with an acetonitrile gradient or was sequenced directly as a mixture. This chemical cleavege produced a large hydrophobic peptide that contained about a 200 amino acid sequence which connected with the Asp-Ala-Pro at residue 70. The elution profile is shown on FIG. 5C.

The remaining, short section of overlapping sequence from between residues 40 to 50 was determined by digesting gelonin without alkylation by Lysc in SDS. This digested away most of the C-terminal part of the material. Then this mixture was digested again by chymotrypsin. The products of this digestion were then separated by HPLC. Sequence analysis of a large pepticle revealed a sequence (SerThrLys) starting about 5 amino acids in from the N terminal end of the molecule. This was useful in that it removed the heterogeneous part of the molecule and allowed for a longer sequence run.

Gelonin protein comprises 258 amino acids, the sequence of which is demonstrated on FIG. 1. The amino acid sequence of gelonin was compared to other known sequences available in sequence data banks (Genbank, PIR, EMBL) to determine whether gelonin has any areas of homology with other proteins. Comparison of the gelonin amino acid sequence with other proteins having known amino acid sequences, demonstrated that the gelonin sequence is unique. Homology of certain portions of the gelonin sequence to portions of other proteins was detected. For instance, gelonin demonstrates a 36.0% homology with alphatrichosanthin from *Trichosanthin kirilowi,* 33.8% homology with Abrin A chain from Indian Licquorice, 35.2% homology with agglutinin precursor from Castor bean, 33.7% homology with Ricin D, A chain from Castor bean and 27.3% homology with antiviral protein (MAP) from *Mirabills jalapa.* A summary of the degree of homology to these and other proteins is shown on FIG. 3.

Hydrophobicity plots shown on FIG. 6A–6E demonstrate a similarity to hydrophobic regions of trichosanthin, Ricin and to other ribosomal inhibiting proteins.

A plot of the hydropathy of the gelonin structure shows a hydrophobic region in residues 35–80 and 150–180. These are areas in which substantial folding of the molecule probably occurs. This similar hydrophobic pattern is also observed for other toxins (see FIGS. 6A–6E) and may suggest that the active enzymatic center may be contained within these folded regions. Therefore, the active enzymatic site may not be found in a linear region of the molecule and these structures may need to be adequately folded to attain the proper enzymatic center.

Utilizing the cDNA of gelonin, recombinant gelonin can be produced. Mutations can be specifically introduced into the molecule in order to provide recombinant gelonin lacking carbohydrate groups which can misdirect gelonin-antibody conjugates. Recombinant gelonin molecules can be produced by site directed mutagenesis to have greater toxic activity than the native molecule, to be more effectively internalized once bound to the cell surface by a carrier such as a monoclonal antibody or a targeting ligand such as IL-2, EGF, IFN, etc., to resist lysosomal degradation and thus be more stable and longer acting as a toxic moiety.

Recombinant gelonin molecules can also be engineered as fusion products to contain other functional modalities to kill cells such as an enzymatic activity, TNF, IFN activity, a second toxic activity, such as diptheria toxin action (wherein said second activity was through a different biological pathway than gelonin), thus creating a "supertoxin" or a toxin with multifunctional actions.

Fusion proteins can be engineered with gelonin to carry drugs such as chemotherapeutic agents or isotopes for radioimaging or radiotherapy. Gelonin peptides may have application as abortofacient agents, immuno suppressive agents, anticancer agents and as antiviral agents (such as an anti-HIV agent).

The following examples provide a detailed description of the preparation, characterization, and amino acid sequence of gelonin. The experimental methods utilized are described in detail in the examples below. These examples are not intended to limit the invention in any manner.

EXAMPLE 1

Purification and Characterization of Gelonin

Gelonin was isolated from the seeds of the plant *Gelonim multiforum* essentially according to the procedure as described (Stirpe, et al. (1980) *J. Biol, Chem* 255 6947–6953). Briefly, gelonin was extracted from the seeds by homogenization in buffered saline solution (pH 7.4). The supernatant was concentrated after dialysis against 5 mM sodium phosphate (pH 6.5) and the gelonin further purified by ion exchange chromatography as described below. The purity of the gelonin toxin was assessed by high pressure liquid chromatography (HPLC) and sodium dodecylsulphate-polyacylamide gel electrophoreseis (SDS-Page). Gelonin toxin migrated as a single band with an approximate molecular weight of 29–30,000 daltons.

Gelonin toxin activity was measured as described in Example 2 by protein synthesis inhibition in a cell-free system.

Seeds of *Gelonium multiflorum* were shelled and the nuts ground in a homogenizer with eight volumes of 0.14 M NaCl containing 5 mM sodium phosphate (pH 7.4). The homogenate was left overnight at 4° C. with continuous stirring, cooled on ice and centrifuged at 35,000 times g for 20 minutes at 0° C. The supernatant was removed, dialyzed against 5 mM sodium phosphate (pH 6.5) and concentrated using a pm10 filter. The sample was layered on a CM-52 ion-exchange column (20×1.5 cm) equilibrated with 5 mM sodium phosphate (pH 6.5). Material which bound to the ion exchange resin was eluted with 400 ml of 0 to 0.3 M linear NaCl gradient at a rate of 25 ml hour at 4° C. Five ml fractions were collected. The fractions were monitored at 280 nm in a spectrophotometer. The gelonin eluted in about fractions 55–70 and was the last major elution peak. These fractions were pooled, dialyzed against 0.1 M NaCl in 0.1 M $Na_2HPO_4$ buffer (pH 7.4). The sample was then applied to a Cibacron blue sepharose column (24×2 cm) previously equilibrated with 0.1 M $Na_2HPO_4$/0.1 M NaCl buffer. The column was washed with 3 column volumes of buffer and eluted with a 400 ml linear salt gradient (from 0.1 M NaCl to 2 M NaCl). Elution of the bound material was monitored by Lowry assay of the column fractions. The fractions containing the single protein peak were pooled and dialyzed overnight at 4° C. against PBS. Gelonin toxin was purified to greater than 97% purity as estimated from silver stained PAGE. The purity and the molecular weight of each preparation was checked on high pressure liquid chromotography using a TSK 3000 gel permeation column with 50 mM sodium phosphate buffer, pH 7.4 and 15% sodium dodecylsulphate-polyacrylamide gel electrophoresis (SDS-page). Gelonin migrated as a single band with an approximate molecular weight of 29–30,000 daltons.

EXAMPLE 2

Assay of Gelonin Activity

The gelonin activity was monitored in a cell-free protein synthesis inhibition assay. The cell-free protein synthesis inhibition assay was performed by sequentially adding to 50 ul rabbit reticulocyte lysate, thawed immediately before use, mixing after each addition, the following components: 0.5 ml of 0.2 M Tris HCl (pH 7.8), 8.9 ml of ethylene glycol, and 0.25 ml of 1 M HCl).

Twenty microliters of a salt-amino acid-energy mixture (SAEM) consisting of: 0.375 M KCl, 10 mM $Mg(CH_3CO_2)_2$, 15 mM glucose, 0.25–10 mM amino acids (excluding leucine), 5 mMATP, 1 mMGTP, 50 mMTris-HCl (pH 7.6), 10 ul Creatinine phosphate-creatinine phosphokinase, 8 ul $[^{14}C]$ leucine (Amersham, 348 mCi/mmol), and adding 1.5 ul of solutions containing varying concentrations of the gelonin mixture. The mixture was incubated for 60 minutes at 30° C. $^{14}C$-leucine incorporation was monitored in an aliquot of the mixture by precipitating synthesized protein on glass fiber filters, washing in 10% TCA and acetone, and monitoring the radioactivity in a Beta-counter using Aquasol scintillation fluid. Utilizing this assay, purified gelonin had a specific activity of $4\times10^9$ U/mg protein. A unit of gelonin activity is the amount of gelonin protein which causes 50% inhibition of incorporation of $[^{14}C]$ leucine into protein in the cell free assay.

EXAMPLE 3

Determination of Gelonin Amino Acid Sequence

The gelonin amino acid sequence was determined by the Edman degradation method using an automated amino acid sequencer as described in European Patent Application No. EP-257735. Large peptides and unfragmented protein were applied to the reverse phase portion of the sequence reaction chamber. Unwanted buffer components were washed off with excess water. The protein or peptide sample was then sequenced by Edman chemistry and the extracted ATZ amino acid derivatives were converted to the PTH form by 25% TFA in $H_2O$ at 65° C. PTH samples were identified by reverse phase analytical separation on a Np 1090 column.

In order to obtain further amino acid sequence, the protein was digested with various proteolytic and chemical agents and then the peptides were purified by high performances liquid chromatography. Gelonin was found quite resistant to the exposure of trypsin (cleaves after arginine and lysine residues) and acetyl trypsin (cleaves only after lysine residue). The protein was found resistant to as much as 5% (w/w) of the enzyme. The resistance of gelonin to the proteolytic enzyme trypsin is not due to a lack of trypsin cleavage sites, since gelonin contains 21 lysine and 12 arginine residues. These results indicate that gelonin is perhaps a rigidly packed molecule which makes it inaccessible to proteolytic enzymes.

Since gelonin was found resistant to cleavage by proteolytic enzymes, chemical cleavage of the protein was examined.

EXAMPLE 4

CNBr Cleavage of Gelonin

Gelonin prepared as in Example 1 was dissolved in 70% formic acid. A crystal of cyanogen bromide was added to the solution. After at least 18 hours the solution was applied to either a small column (0.15 cm×5 cm) reverse phase (J. T. Baker; 15 cm C-1B bonded phase Cat II 7191-02) or analytical (4.6×100 mm) reversed phase column. A gradient elution of 1 to 70% n propanol with 1% TFA in water produce 5 peaks as shown on FIG. 6. Each of the peaks were sequenced and also used for further digestion by enzymes to piece together the entire sequence. Peak 1 was sequenced directly and gave a sequence starting with a Phe (F) that ran for 38 residues and ending with a Glu (E). This sequence was confirmed by mass spectroscopy and Lysc digestions of this isolated peptide. Peak 2 was sequenced directly and gave a sequence starting with a Val (V) that ran for 47 cy and was not interruptable after the ala at cy 47. Peak 3 was sequenced and gave the same sequence as peak 2. SDS gels of peaks 2 and 3 as well as Lysc digestion of peaks 2 and 3 showed that peak 3 contained the C-terminal CNBr peptide as well. Subsequent trypsin digestion of gelonin produced a peptide that connected these two CNBr peptide sequences. This trypsin peptide when sequenced gave the sequence TSGANGMFSEAVELER. Peak 4 and 5 both gave the N-terminal sequence GLDT . . . . This was used for some digestion by Lysc, ⅛, to give peptides from its C-terminal end.

EXAMPLE 5

Enzymatic Digestion of CNBr Cleaved Gelonin

Samples of whole protein or CNBr fragments were digested with Lysyl endopeptidase (Wako Chemical Dallas, Tex.) in 0.1% SDS 100 mmTris pH 8.0 or Staphylococcus Aureus Protease (Pierce) in.1% SDS or Trypsin (Sigma) in 0.1% Tween 20. Digestion mixtures were separated by HPLC and collected peptides were sequenced on the prototype sequence use gas-phase Edman sequencing methods.

EXAMPLE 6

Amino Acid Sequence of Gelonin

A total of 258 amino acid residue sequences were obtained following analysis of the CNBr fragments obtained in Example 3. FIG. 1 shows the amino acid sequence of gelonin. Gelonin contains a total of approximately 258 amino acid residues. The DNA sequence was deduced from this amino acid sequence. The degenerate DNA sequence is shown on FIG. 2. Those skilled in the art will recognize that fragments and derivatives of either the gelonin amino acid sequence or the DNA sequence coding for gelonin may inhibit cellular protein synthesis but not bind to a cell surface receptor.

The invention now being fully described, it will be apparent to one of ordinary skill in the art that many changes and modifications can be made thereto without departing from the spirit or scope of the invention as set forth below.

What is claimed as new and is desired to be covered under Letters Patent is:

1. Substantially pure gelonin toxin having the amino acid sequence:

10
GlyLeuAspThrValSerPheSerThrLys
20
GlyAlaThrTyrIleThrTyrValAsnPhe
30
LeuAsnGluLeuArgValLysLeuLysPro
40
GluGlyAsnSerHisGlyIleProLeuLeu
50
ArgLysGlyAspAspProGlyLysCysPhe
60
ValLeuValAlaLeuSerAsnAspAsnGly
70
GlnLeuAlaGluIleAlaIleAspValThr
80
SerValTyrValValGlyTyrGlnValArg
90
AsnArgSerTyrPhePheLysAspAlaPro
100
AspAlaAlaTyrGluGlyLeuPheLysAsn
110
ThrIleLysAsnProLeuLeuPheGlyGly
120
LysThrArgLeuHisPheGlyGlySerTyr
130
ProSerLeuGluGlyGluLysAlaTyrArg
140
GluThrThrAspLeuGlyIleGluProLeu
150
ArgIleGlyIleLysLysLeuAspGluAsn
160
AlaIleAspAsnTyrLysProThrGluIle
170
AlaSerSerLeuLeuValValIleGlnMet
180
ValSerGluAlaAlaArgPheThrPheIle
190
GluAsnGlnIleArgAsnAsnPheGlnGln
200
ArgIleArgProAlaAsnAsnThrIleSer
210
LeuGluAsnLysTrpGlyLysLeuSerPhe
220
GlnIleArgThrSerGlyAlaAsnGlyMet
230
PheSerGluAlaValGluLeuGluArgAla
240
AsnGlyLysLysTyrTyrValThrAlaVal
250
AspGlnValLysProLysIleAlaLeuLeu
260
LysPheValAspLysAspProGlu or a fragment or derivative thereof, said fragment or derivatives or having an activity which inhibits cellular protein synthesis but does not bind to a cell surface receptor.

2. A DNA sequence of the formula:

| | | | | | | |
|---|---|---|---|---|---|---|
| GGNYTNGAYA | CNGTNWSNTT | YWSNACNAAR | GGNGCNACNT | AYATHACNTA | YGTNAAYTTY | 60 |
| YTNAAYGARY | TNMGNGTNAA | RYTNAARCCN | GARGGNAAYW | SNCAYGGNAT | HCCNYTNYTN | 120 |

-continued

| | | | | | | |
|---|---|---|---|---|---|---|
| MGNAARGGNG | AYGAYCCNGG | NAARTGYTTY | GTNYTNGTNG | CNYTNWSNAA | YGAYAAYGGN | 180 |
| CARYTNGCNG | ARATHGCNAT | HGAYGTNACN | WSNGTNTAYG | TNGTNGGNTA | YCARGTNMGN | 240 |
| AAYMGNWSNT | AYTTYTTYAA | RGAYGCNCCN | GAYGCNGCNT | AYGARGGNYT | NTTYAARAAY | 300 |
| ACNATHAARA | AYCCNYTNYT | NTTYGGNGGN | AARACNMGNY | TNCAYTTYGG | NGGNWSNTAY | 360 |
| CCNWSNYTNG | ARGGNGARAA | RGCNTAYMGN | GARACNACNG | AYYTNGGNAT | HGARCCNYTN | 420 |
| MGNATHGGNA | THAARAARYT | NGAYGARAAY | GCNATHGAYA | AYTAYAARCC | NACNGARATH | 480 |
| GCNWSNWSNY | TNYTNGTNGT | NATHCARATG | GTNWSNGARG | CNGCNMGNTT | YACNTTYATH | 540 |
| GARAAYCARA | THMGNAAYAA | YTTYCARCAR | MGNATHMGNC | CNGCNAAYAA | YACNATHWSN | 600 |
| YTNGARAAYA | ARTGGGGNAA | RYTNWSNTTY | CARATHMGNA | CNWSNGGNGC | NAAYGGNATG | 660 |
| TTYWSNGARG | CNGTNGARYT | NGARMGNGCN | AAYGGNAARA | ARTAYTAYGT | NACNGCNGTN | 720 |
| GAYCARGTNA | ARCCNAARAT | HGCNYTNYTN | AARTTYGTNG | AYAARGAYCC | NGAR | 774 |

wherein

| | | |
|---|---|---|
| R = A or G | K = G or T | N = any |
| Y = C or T | M = A or C | S = C or G |
| B = C, G, or T | V = A, C, or G | W = A or T |
| D = A, G, or T | H = A, C, or T | X = unknown |

or a fragment or derivative thereof, said fragment or derivative coding for gelonin or for a polypeptide having an activity which inhibits cellular protein synthesis but does not bind to a cell surface receptor.

* * * * *

UNITED STATES PATENT AND TRADEMARK OFFICE

CERTIFICATE OF CORRECTION

PATENT NO. : 5,631,348

DATED : MAY 20, 1997

INVENTOR(S) : Michael G. Rosenblum

It is certified that error appears in the above-identified patent and that said Letters Patent is hereby corrected as shown below:

In Figure 1, amino acid residue number 41, "S", should read --R--.

In Figure 2A, amino acid residue number 41, "Ser", should read --Arg--.

In Figure 2A, nucleotides 121-122, "WS", should read --MG--.

In Figure 3, amino acid residue number 41 within the sequence "L--SKG" should read --L--RKG--.

In Column 1, line 34, "*Biol, Res, Modif,*" should read --*Biol. Res. Modif.*--.

In Column 1, line 41, "*Br, Med,*" should read --*Br. Med.*--.

In Column 1, line 50, "62:93-117. Vitetta" should read --62:93-117; Vitetta--.

In Column 1, line 50, "*Immun. Rev,*" should read --*Immuno. Rev.*--.

In Column 1, line 51, "*Immun. Rev*, 92" should read --*Immun. Rev.* 62--.

UNITED STATES PATENT AND TRADEMARK OFFICE

CERTIFICATE OF CORRECTION

PATENT NO. : 5,631,348
DATED : MAY 20, 1997
INVENTOR(S) : Michael G. Rosenblum

It is certified that error appears in the above-identified patent and that said Letters Patent is hereby corrected as shown below:

In Column 2, line 24, "*J. Natl, Cancer*" should read --*J. Natl. Cancer*--.

In Column 2, line 48, "*Cancer Res,*" should read --*Cancer Res.*--.

In Column 2, line 55, "*Protein Res,*" should read --*Protein Res.*--.

In Column 2, line 61, "efficiently" should read --efficiency--.

In Column 3, line 21, "demonstrates" should read --demonstrate--.

In Column 3, line 22, "Staphyloccus" should read --*Staphylococcus*--.

In Column 3, line 24, "demonstrates" should read --demonstrate--.

In Column 3, line 38, "*Gilonin*" should read --*Gelonium*--. (second occurrence)

In Column 3, line 53, "cleaveges" should read --cleavages--.

In Column 3, line 57, "soluable" should read --soluble--.

UNITED STATES PATENT AND TRADEMARK OFFICE

CERTIFICATE OF CORRECTION

PATENT NO. : 5,631,348

DATED : MAY 20, 1997

INVENTOR(S) : Michael G. Rosenblum

It is certified that error appears in the above-identified patent and that said Letters Patent is hereby corrected as shown below:

In Column 3, line 60, "staphlococcal" should read --Staphylococcal--.

In Column 4, line 6, "fragmants" should read --fragments--.

In Column 4, line 9, "fragmants" should read --fragments--.

In Column 4, line 11, "Staphylococcus Aureus Protease" should read --*Staphylococcus aureus* protease--.

In Column 4, line18, "cleaveges. The" should read --cleavages, the--.

In Column 4, line 32, "NaCl, mm EDTA" should read --NaCl, 1 mm EDTA--.

In Column 4, line 35, "colulmn" should read --column--.

In Column 4, line 37, "cleavege" should read --cleavage--.

In Column 4, line 57, "sequences. demonstrated" should read --sequences demonstrated--.

In Column 4, line 62, "Licquorice" should read --Liquorice--.

UNITED STATES PATENT AND TRADEMARK OFFICE

CERTIFICATE OF CORRECTION

PATENT NO. :5,631,348
DATED :MAY 20, 1997
INVENTOR(S) :Michael G. Rosenblum

It is certified that error appears in the above-identified patent and that said Letters Patent is hereby corrected as shown below:

In Column 5, line 46, "*Gelonim*" should read --*Gelonium*--.

In Column 5, line 48, "*J. Biol, Chem*" should read --*J. Biol. Chem.*--.

In Column 5, line 61, "*multiflorum*" should read --*multiforum*--.

In Column 6, line 20, "chromotography" should read --chromatography--.

In Column 6, line 40, "5mMATP, 1 mMGTP, 50 mMTris-HCl" should read --5 mM ATP, 1 mM GTP, 50 mM Tris-HCl--.

In Column 7, line 3, "performances" should read --performance--.

In Column 7, line 25, "reversed" should read --reverse--.

In Column 7, line 27, "produce" should read --produced--.

In Column 7, line 35, "interruptable after the ala" should read --interruptible after the Ala--.

In Column 7, line 52, "100 mmTris" should read --100 mM Tris--.

UNITED STATES PATENT AND TRADEMARK OFFICE

CERTIFICATE OF CORRECTION

PATENT NO. : 5,631,348

DATED : MAY 20, 1997

INVENTOR(S) : Michael G. Rosenblum

It is certified that error appears in the above-identified patent and that said Letters Patent is hereby corrected as shown below:

In Column 7, line 53, "Staphylococcus Aureus Protease" should read --*Staphylococcus aureus* protease--.

In Column 7, line 53, "in.1%" should read --in 0.1%--.

In Column 7, line 56, "use" should read --using--.

In Column 8, line 59-60 (Claim 1), "derivatives or having" should read --derivative having--.

Signed and Sealed this

Ninth Day of February, 1999

Attest:

*Acting Commissioner of Patents and Trademarks*

*Attesting Officer*